United States Patent

Hirai et al.

[11] Patent Number: 6,127,528
[45] Date of Patent: Oct. 3, 2000

[54] PROCESS FOR ADSORBING AND REMOVING TUMOR NECROSIS FACTOR-α

[75] Inventors: Fumiyasu Hirai, Amagasaki; Nobutaka Tani, Osaka; Takashi Asahi, Kobe, all of Japan

[73] Assignee: Kanegafuchi Kagaku Kogyo Kabushiki Kaisha, Osaka, Japan

[21] Appl. No.: 09/283,964

[22] Filed: Apr. 2, 1999

Related U.S. Application Data

[62] Division of application No. 08/894,052, Aug. 12, 1997, abandoned.

[30] Foreign Application Priority Data

Feb. 16, 1995 [JP] Japan ........................... 7-28129

[51] Int. Cl.$^7$ .............. C07K 1/22; C07K 1/14; C07K 14/00; A61K 38/19
[52] U.S. Cl. .................. 530/415; 530/351; 530/412; 530/417; 930/144
[58] Field of Search ................ 530/412, 415, 530/351; 930/144

[56] References Cited

U.S. PATENT DOCUMENTS

| | | | |
|---|---|---|---|
| 4,997,874 | 3/1991 | Asano et al. | 524/3 |
| 5,403,917 | 4/1995 | Boos | 530/351 |
| 5,679,775 | 10/1997 | Boos et al. | 530/351 |

FOREIGN PATENT DOCUMENTS

| | | |
|---|---|---|
| 64-48272 | 3/1989 | Japan . |
| 1-119264 | 5/1989 | Japan . |
| 1-171638 | 7/1989 | Japan . |
| 1-181875 | 7/1989 | Japan . |
| 6-211900 | 8/1994 | Japan . |

OTHER PUBLICATIONS

Database CAPLUS, AN: 1985:543086, JP 60088041, May 17, 1985.
Database CAPLUS, AN: 1968:478047; Zundel, G. Kunstst. Rundsch., 15(4), 166–71.
Database CAPLUS, AN: 1992:175620; J. Membr. Sci., 64(3), 255–62.
Database CAPLUS, AN:2755; JP 58124798.

*Primary Examiner*—Michael Borin
*Attorney, Agent, or Firm*—Kubovcik & Kubovcik

[57] ABSTRACT

The present invention relates to an adsorbent being capable of efficiently removing tumor necrosis factor-α (TNF-α) in a body fluid, an adsorber using the adsorbent and a process for adsorbing and removing TNF-α, namely an adsorbent of TNF-α, wherein onto a water-insoluble carrier a compound having a functional group represented by the formula (I):

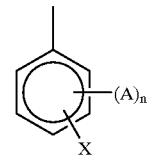

(I)

wherein $X^-$ is an anionic functional group, A is a substituent group except for the anionic functional group, n is an integer of 0 to 4 and in case n is at least 2, groups A, the number of which is n, may be the same or different from each other; a process for adsorbing and removing TNF-α, which comprises coming the adsorbent into contact with a body fluid; and an adsorber for adsorbing TNF-α wherein a vessel having an inlet and an outlet for a body fluid and being equipped with a means for preventing the adsorbent from flowing to the outside of the vessel, is charged with the adsorbent.

5 Claims, 4 Drawing Sheets

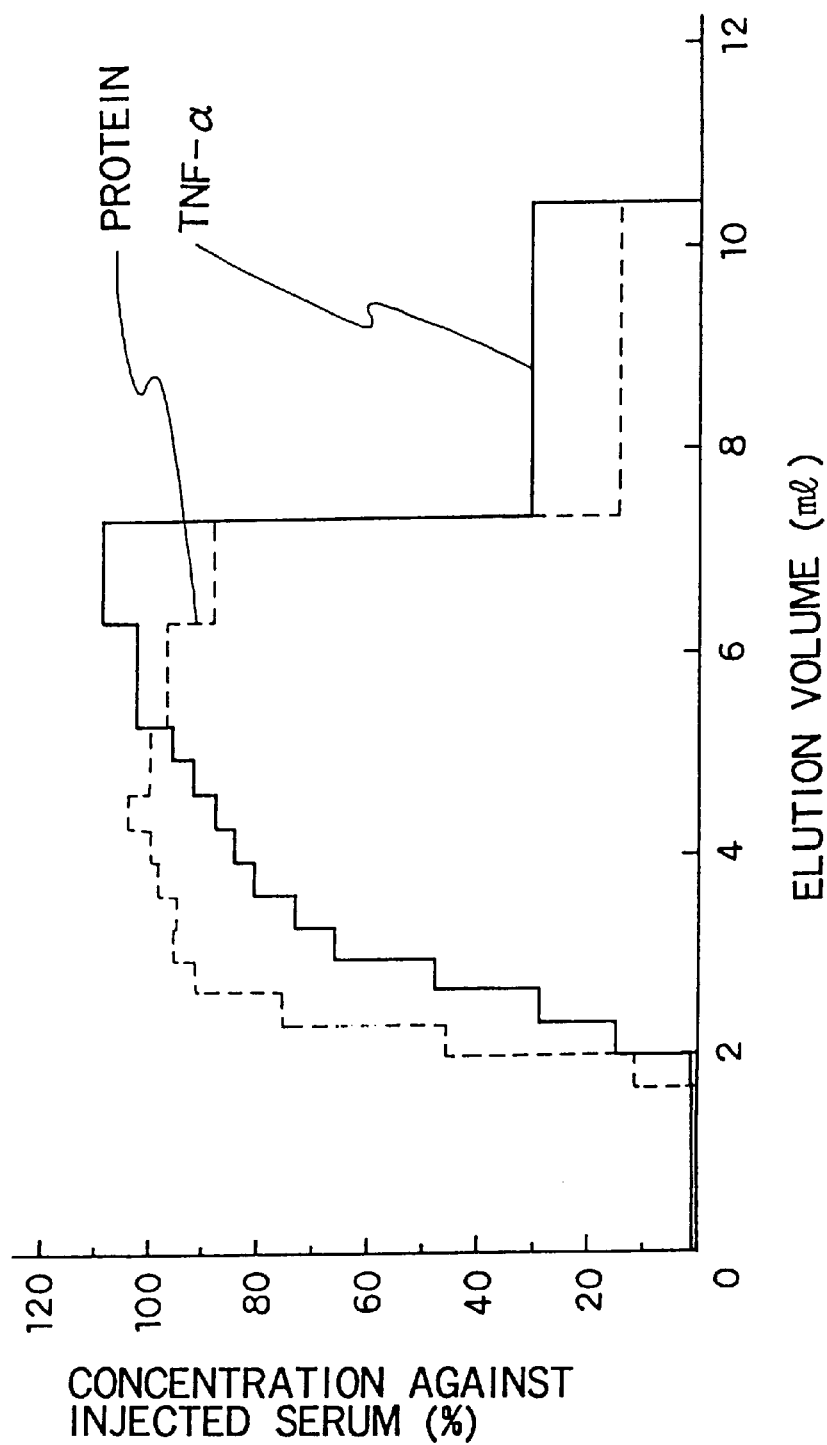

PROCESS FOR ADSORBING AND REMOVING TUMOR NECROSIS FACTOR-α

This application is a division of application Ser. No. 08/894,052, filed Aug. 12, 1997, now abandoned.

TECHNICAL FIELD

The present invention relates to an adsorbent for tumor necrosis factor-α (hereinafter referred to as "TNF-α"), a process for adsorbing and removing TNF-α by using the adsorbent, and an adsorber for TNF-α by using the adsorbent.

BACKGROUND ART

Septicemia means a condition wherein a generalized inflammatory reaction is caused because of an infection occurred somewhere in body. When this inflammatory symptom progresses, a shock symptom occurs (septic shock) and an organopathy occurs (organ failure), and further, a patient comes to have severe conditions such as a multiple organ failure.

Typical substances which occur an inflammation from an infection in this way are various kinds of cytokines and activated complements which are produced by the presence of an endotoxin in a surface of Gram-negative bacterium, and TNF-α is regarded as the most important from points of view that a blood level of TNF-α among such cytokines increases at first and that TNF-α promotes production of other cytokines.

Septicemia can be caused by Gram-positive bacterium as well as by Gram-negative bacterium. In this case, it is considered that septicemia is caused by a cytokine such as TNF-α, or the like which is produced by various stimulations owing to local infections even if the endotoxin is not present. Also, in septicemia, when a blood level of TNF-α is kept high, prognosis thereof becomes bad, and the level of TNF-α reflects well a degree of severe condition ("Shucyu Ciryo" 6(2), 115–123 (1994)).

As a conventional therapy for such septicemia, there is a therapy wherein an antibiotic is administrated as an infection measures or a therapy wherein γ-globulin is administrated in order to activate resistance to the infection. However, a mortality rate is still high. So, it is desired from a medical standpoint to remove from a body fluid TNF-α which is regarded as the most important among cytokines which occur inflammation.

It is known that a blood level of TNF-α becomes high in agreement with the condition of a disease in other diseases except for septicemia such as IBD (inflammatory bowel disease), SLE (systemic lupus erythematosus), the Kawasaki disease, and the like wherein an immunity abnormality is assumed as a cause of the diseases, and further, it is known that a concentration of TNF-α in joint liquid rises in the case of RA (rheumatoid arthritis) ("Nippon Rinsho", 48, irregularly, 304–311, (1990)). Accordingly, for these diseases, a therapy to remove TNF-α from a body fluid is considered.

Japanese Unexamined Patent Publication No. 211900/1994 (an application by B. Brown Merzgen Aktiengesellschaft) discloses an adsorbent for removing TNF-α from a body fluid, which comprises a porous carrier to which a polyanion polymer is covalently bonded and in Example thereof a porous carrier is employed, to which a dextran sulfate is bonded.

However, it has been proved by the inventors of the present invention that in the porous carrier to which a dextran sulfate is covalently bonded, which is described in Japanese Unexamined Patent Publication No. 211900/1994, interaction between TNF-α and the dextran sulfate is weak and that when a liquid containing TNF-α is flowed into a column which was charged with the porous carrier to which the dextran sulfate is bonded, TNF-α is not adsorbed and it is only eluted from the column later.

Also it has been proved similarly that preferable results can not be obtained in an employment of a sulfonated polysaccharide such as a heparin or chondroitin sulfate, instead of the dextran sulfate, a polypeptide such as polyglutamic acid or polyaspartic acid, and a nucleic acid, and further a polyacrylic acid and polyvinylsulfate.

DISCLOSURE OF THE INVENTION

The present invention has been accomplished in order to improve disadvantages of the conventional adsorbent comprising a porous carrier to which a polyanion polymer is bonded as mentioned above and to give an adsorbent which can adsorb and remove TNF-α selectively from a body fluid, in particular, blood, plasma or serum.

The invention relates to an adsorbent of TNF-α wherein onto a water-insoluble carrier is immobilized a compound having a functional group represented by the formula (I):

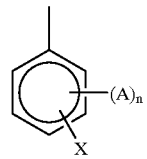

(I)

wherein X is an anionic functional group; A is a substituent group except for the anionic functional group; n is an integer of 0 to 4 and in case n is at least 2, groups A, the number of which is n, may be the same or different from each other (claim 1), the adsorbent of claim 1, wherein X is sulfonic acid group (claim 2), the adsorbent of claim 1, wherein X is sulfuric ester group (claim 3), the adsorbent of claim 1, wherein the compound having a functional group of the formula (I) has at least two functional groups of the formula (I) in a molecule (claim 4), the adsorbent of claim 4, wherein the compound having at least two functional groups of the formula (I) in a molecule is polystyrenesulfonic acid (claim 5), the adsorbent of claim 1, wherein the water-insoluble carrier is hydrophilic (claim 6), the adsorbent of claim 6, wherein the water-insoluble carrier has hydroxyl group (claim 7), the adsorbent of claim 1, wherein the water-insoluble carrier is porous (claim 8), a process for adsorbing and removing TNF-α, which comprises coming the adsorbent of claim 1 into contact with a body fluid containing TNF-α (claim 9), an adsorber for adsorbing TNF-α, wherein a vessel having an inlet and an outlet for a body fluid and being equipped with a means for preventing the adsorbent from flowing to the outside of the vessel is charged with the adsorbent of claim 1 (claim 10), and use of a compound having a functional group represented by the formula (I):

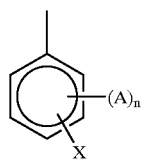

(I)

wherein X is an anionic functional group, A is a substituent group except for the anionic functional group, n is an integer of 0 to 4 and in case n is at least 2, groups A, the number of which is n, may be the same or different from each other, the compound being immobilized onto a water-insoluble carrier, for the manufacture of an adsorbent for a new and inventive adsorption of TNF-α (claim 11).

A body fluid in the present invention means blood, plasma, serum, ascites, lymph, synovial fluid, a fractionated component obtained from these fluids, or a liquid component from the other living body.

TNF-α is a simple protein having a molecular weight of 17 kDa which comprises 157 amino acids and usually forms trimer. Accordingly a molecular weight of the trimer is approximately 51,000.

BRIEF EXPLANATIONS OF THE DRAWINGS

FIG. 4 is a graph showing the change of the concentration of TNF-α and protein in the elution liquid when serum containing TNF-α was flowed through the adsorber for adsorbing TNF-α of COMPARATIVE EXMAPLE 3, wherein a column is charged with CELLULOFINE GC-700m onto which sodium dextran sulfate is immobilized.

BEST MODE FOR CARRYING OUT THE INVENTION

Figure 1:
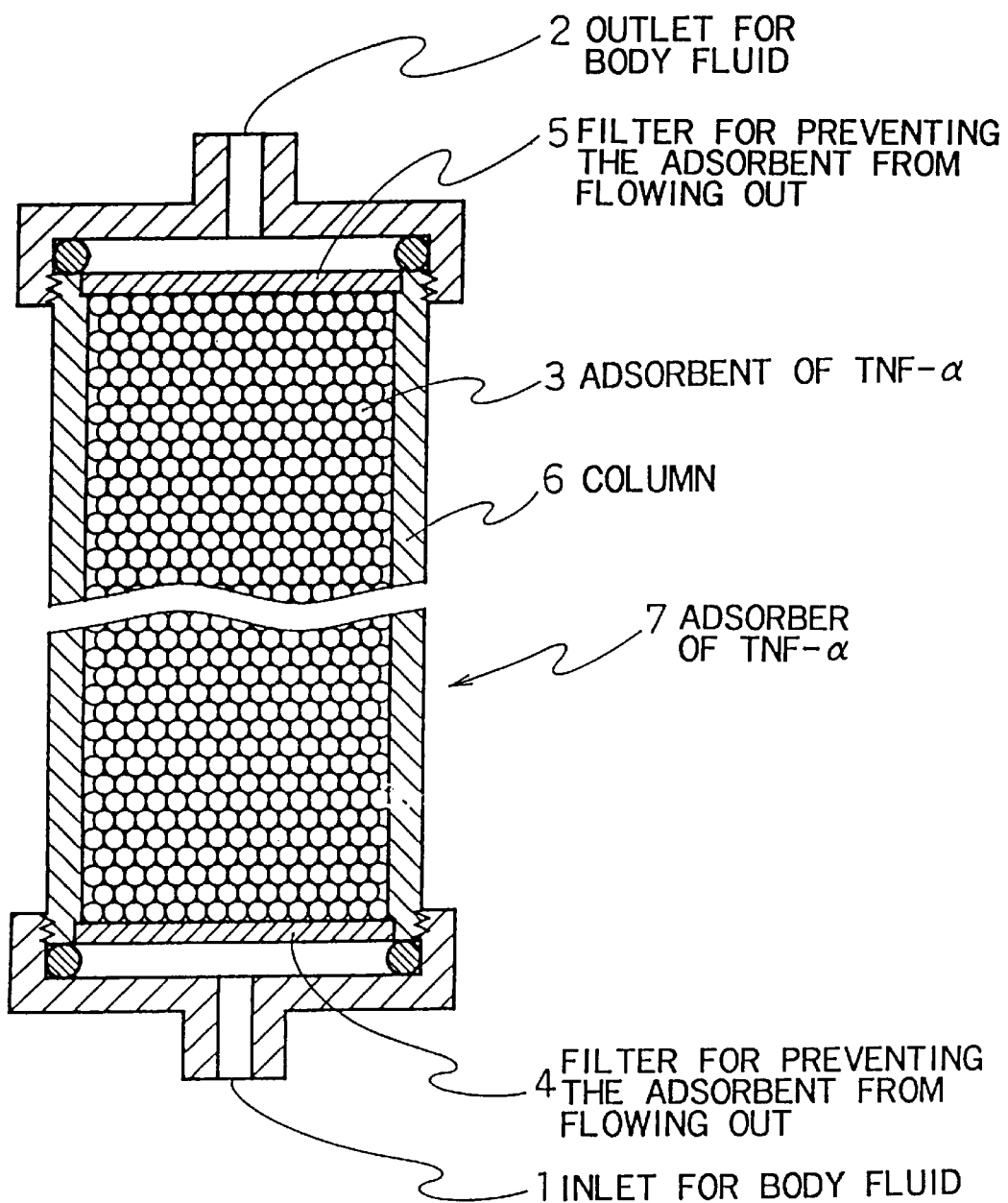
FIG. 1 is a schematic cross section of one example of the adsorber for adsorbing TNF-α of the present invention.

A compound used in the present invention, which is immobilized onto a water-insoluble carrier and has a functional group represented by the formula (I):

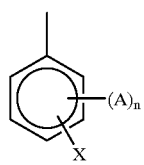

(I)

wherein X is an anionic functional group, A is a substituent group except for the anionic functional group, n is an integer of 0 to 4 and in case n is at least 2, groups A, the number of which is n, may be the same or different from each other, as mentioned above, is a compound which has benzene ring to which one anionic functional group is bonded wherein at the remaining four positions of benzene ring hydrogen atom or the substituent group except for the anionic functional group may be bonded. Also, at a part of four positions of benzene ring the substituent group except for the anionic functional group can be bonded. When there are at least two of the above mentioned substituent groups, they may be the same or different from each other.

The anionic functional group is a functional group that can be charged negatively at a pH value around neutral. The anionic functional group is not limit in particular so long as it has such character. As the representative examples of such anionic functional group, there are, for example, carboxyl group, sulfonic acid group, sulfuric acid group, a silanol group, phosphoric ester group, phenolic hydroxyl group, and the like, however, it is not limited thereto. Among them, sulfonic acid group and sulfuric acid group are preferable.

The substituent group (A) which is bonded to benzene ring of the formula (I) is not limited so long as it is the substituent group except for the anionic functional group, and can be an alkyl group such as methyl group or ethyl group or an aromatic group such as phenyl group and can be a group which does not contain any carbon atom, such as nitro group or hydroxyl group.

As the concrete examples of the compound having the functional group of the formula (I) which is a functional group represented by the formula (II):

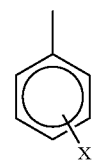

(II)

wherein X is the same as defined above, there are, for instance, dihydroxy benzene, aminophenol, hydroxybenzoic acid (salicylic acid), phthalic acid, sulfobenzoic acid, aminobenzoic acid, benzenedisulfonic acid, aminobenzenesulfonic acid (sulfanilic acid), phenolsulfonic acid, and the like, however, it is not limited thereto. Among them, sulfobenzoic acid, benzene disulfonic acid, aminobenzenesulfonic acid and phenol sulfonic acid are preferable because they have sulfonic acid group which is strong acid.

As the concrete examples, of the compound having the functional group of the formula (I) which is a functional group represented by the formula (III):

(III)

the formula (IV):

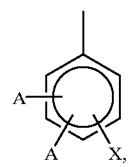

(IV)

the formula (V):

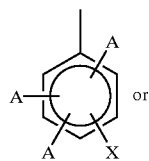

or the formula (VI):

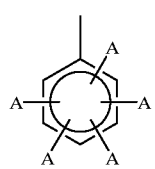

wherein X and A are the same as defined above and when at least two groups of A are bonded, they may be the same or different from each other, there are, for instance, aminohydroxybenzenesulfonic acid, methylsalicylic acid, chloromethyl-nitrobenzene sulfonic acid, and the like, however, it is not limited thereto.

The compound having the functional group of the formula (I) can be a compound having one of the functional group in a molecule or can be a compound having at lesat two of the functional groups in a molecule. The compound that has at least two functional groups of the formula (I) is preferable because it has high affinity to TNF-α and many of the functional groups can be easily introduced into an unit volume of solid substance. Particularly a compound having a molecular weight of at least 1000 is more preferable because it has high affinity to TNF-α and many of the functional groups can be easily introduced into an unit volume of solid substance.

When the compound has at least two functional groups of the formula (I), these functional groups may be the same or different from each other.

As the concrete examples of such compound having at least two functional groups in a molecule, there are, for example, polystyrenesulfonic acid, polystyrenephosphoric acid, and the like, however, it is not limited thereto. Among them, polystyrene sulfonic acid is preferable because it has sulfonic acid group which is strong acid.

As a water-insoluble carrier used in the present invention, there are, for instance, an inorganic carrier such as glass beads or silica gel, a water-insoluble carrier comprising a synthetic polymer such as polyvinyl alcohol, saponificated ethylene-vinyl acetate copolymer, poly(meta)acrylate such as polymethyl methacrylate, poly(meta)acrylic acid, polyacrylamide, polystyrene, polyacrylic acid-grafted polyethylene or polyacrylamide-grafted polyethylene; an organic carrier comprising a polysaccharide such as crystalline cellulose, cellulose, agarose, dextran or chitosan; and further a composite carrier obtained from a combination of the above-mentioned compounds such as an organic-organic carrier and organic-inorganic carrier, however, it is not limited thereto.

These carriers may be used alone or may be used by combining arbitrarily 2 or more kinds thereof. Among them, a hydrophilic carrier is preferable because non-specific adsorption is comparatively a little and selective adsorption of TNF-α is good.

The hydrophilic carrier mentioned above means a carrier having a contact angle of at most 60 degrees with water. The contact angle is that of a compound constituting the carrier which is made to be in the form of a flat plate. Examples of such carrier include carriers comprising a polysaccharide such as cellulose, chitosan, agarose, dextran, or the like; a hydrophilic synthetic polymer such as poly(vinyl alcohol), saponified ethylene-vinyl acetate copolymer, polyacrylamide, poly(acrylic acid), poly(methacrylic acid), poly(acrylic acid-grafted polyethylene), poly(acrylamide-grafted polyethylene), or the like; and glass.

Among the water-insoluble carriers mentioned above, particularly a hydrophilic carrier having hydroxyl group is excellent in ability for adsorption and selectively. Among them, a porous cellulose gel is the most preferable one for the carrier used in the present invention because of such superior points as follows:

① The carrier of the porous cellulose gel is hardly destroyed or generates finely devided particles by the operation of agitation, and the like because of a relatively high mechanical strength and toughness. The carrier is neither compacted nor clogged up when a column is charged therewith and a body fluid is passed through the column at a high flow rate. Further, the pore structure hardly changes by high-pressure steam sterilization.

② The carrier is hydrophilic since the gel is constituted by cellulose. There are present many hydroxyl groups available for bonding a ligand, and non-specific adsorption is little.

③ If volume of porosity is enlarged, comparable adsorption volume can be obtained to a soft gel since the strength is relatively high.

④ Safty is high compared to a synthetic macromolecular gel, and the like.

The adsorbent of the present invention can adsorb TNF-α only at the outer surface, however, in order to adsorb more TNF-α, it is preferable to have a lot of pores of suitable size, that is, the adsorbent is porous. In order to adsorb efficiently TNF-α (a molecular weight of trimer: approximately 51,000), it is preferable that TNF-α can enter the pores with somewhat high probability and enter of other proteins do not occur as little as possible.

Although a mercury porosimetry is most frequently used for measuring a pore size, in the porous water-insoluble carrier used in the invention, the mercury porosimetry cannot be applied so often since structure of the carrier is changed on drying. Accordingly, it is suitable to employ a molecular weight of exclusion limit as a measure of the pore size of the pore.

The term "a molecular weight of exclusion limit" means the minimum molecular weight of the molecule wherein a molecule cannot enter a pore (i. e. the molecule is excluded) in a gel permeation chromatography (written by Hiroyuki Hatano and Toshihiko Hanai, "Experimental High Performance Liquid Chromatography", Kagaku Dojin Co., Ltd.).

Generally the molecular weight of exclusion limit for a globular protein, dextran, polyethylene glycol, or the like has been quite studied, and in the carrier used in the invention, it is suitable to employ a value obtained using the globular protein.

Since the molecular weight of trimer TNF-α is approximately 51,000, when the carrier having a molecular weight of exclusion limit of less than $5 \times 10^4$ is used, the amount of adsorbing and removing TNF-α is low and the practicability is dcreased. Accordingly, the preferable molecular weight of exclusion limit of the carrier used for TNF-α is at least $5 \times 10^4$. No problems is occurred so long as plasma or serum is used as a body fluid even if the molecular weight of exclusion limit is over $5 \times 10^6$. However, in case blood is used as a body fluid, there is tendency that a rate of adhesion of platelet increases when the molecular weight of exclusion limit is over $5 \times 10^6$. Accordingly, in case the adsorbent of the invention is applied to a homocatharsis system by direct hemo-perfusion (DHP), an efficient ability of it cannot be necessarily exhibited. On the other hand, in case the molecular weight of exclusion limit is at most $5 \times 10^6$, no serious trouble is particularly caused by any usage. Thus it is desirable that the molecular weight of exclusion limit is at most $5 \times 10^6$ in order to be able to use in many uses or usages.

From the viewpoint of an adsorption ability per unit volume of the adsorbent, it is preferable that the adsorbent has many pores on its surface and it is preferable that a pore volume is at least 20% and a specific surface area is at least 3 m²/g. A form of the carrier can be arbitrary such as granular, fiber or hollow.

Further, it is preferable that there is a functional group on the carrier surface, which can be used for immobilizing a ligand. As the representative examples of such functional group, there are, for instance, hydroxyl group, amino group, aldehyde group, carboxyl group, thiol group, a silanol group, amide group, epoxy group, a halogen group, succinylimide group, acid anhydrous group, and the like.

As the water-insoluble carrier to be used in the invention, each of a hard carrier and a soft carrier can be used. It is important that a column does not be clogged with the carrier when it is charged with the carrier and a fluid passes therethrough in order to use the carrier as an adsorbent for extracorporeal circulation treatment. Since sufficient mechanical strength is needed to satisfy the above requirement, it is more preferable that the carrier is the hard carrier. The term "hard carrier" means, in case that a gel, for example, is a granulated gel as shown in REFERENCE EXAMPLE 1 mentioned below, a carrier which has a linear relationship between a pressure loss ΔP and a flow rate up to 0.3 kg/cm² of pressure loss when a cylindrical column is charged uniformly with the gel and an aqueous fluid is passed through the column.

The adsorbent of the present invention can be obtained by immobilizing the compound having a functional group of the formula (I) onto the water-insoluble carrier, and as an immobilizing method various known methods can be used without a special limit. As the representative methods, there are, for instance, ① a method wherein a compound which does not contain an anionic functional group X is immobilized onto a solid substance (the water-insoluble carrier), and then an anionic functional group X is introduced, ② a method wherein a compound which contains an anionic functional group X is immobilized onto the solid substance, and the like.

As a method for immobilizing these compounds onto the solid substance in the method of ① and ②, there is a method by means of physical adsorption, a method by means of ionic bond, a method by means of covalent bond, or the like and any method can be used. Since it is important that the compound having an anionic functional group is not released for storage and stability of the adsorbent, the method by means of covalent bond, which is possible to make a strong immobilization, is preferable.

As the representative example of the method for introducing X in the method ①, there is a method for introducing sulfonic acid group by treating with concentrated sulfuric acid or chlorosulfonic acid.

On the other hand, when the compound having at least two functional groups of the formula (I) in a molecule is immobilized, there is, ③ a method for graft polymerizing on the solid substance except for the above mentioned methods ① and ②.

An amount of the compound having a functional group of the formula (I), which is immobilized onto the water-insoluble carrier, can be measured as an amount of the anionic functional group by titration. As an amount immobilized, when, for example, the water-insoluble carrier is granular, it is preferable that it is at least 0.01 mmole per 1 ml of sedimentation volume. When it is less than that, an amount of TNF-α which can be adsorbed extremely reduces, and the resulting adsorbent cannot be used practically.

There are various kinds of processes for adsorbing and removing TNF-α in a body fluid by coming a body fluid into contact with the adsorbent wherein the compound having a functional group of the formula (I) is immobilized onto the water-insoluble carrier. As the representative processes, there are, for instance, a process which comprises removing a body fluid, storing it in a bag, mixing the adsorbent therewith to adsorb and remove TNF-α, and filtrating the adsorbent to obtain the body fluid from which TNF-α is removed, a process which comprises charging a vessel having an inlet and an outlet for a body fluid and being equipped with a filter through which a body fluid can pass and the adsorbent cannot pass, at the outlet, preferably at the outlet and the inlet, with the adsorbent, and flowing the body fluid therethrough, and the like. Any processes can be used. With respect to the latter process, however, the operation thereof is simple, and TNF-α can be removed efficiently on-line from a body fluid of a patient by incorporating the latter process into extracorporeal circulation cycle. Accordingly, the adsorbent of the invention is suitable for this process.

In case a column is charged with the adsorbent to use, any adsorbent can be used unless it is fine powder, and it is preferable that a distribution of particle size is narrow so long as plasma or serum is employed as a body fluid. However, it is preferable that the adsorbent has enough space wherein a cell contained in blood can pass freely when blood is flowed therethrough. For example, when the adsorbent is granular, a fine powder is not preferable as mentioned above, and a particle having a particle size of at least 100 μm is preferable. Further, the adsorbent wherein a particle having a too large or too small particle size is removed is preferable, and the adsorbent wherein an average of particle size is in a range from 100 μm to 1000 μm and a distribution of particle size is narrow, is more preferable. When the adsorbent is fiber and hollow, it is preferable that an inner diameter is at least 5 μm. In case the adsorbent is fiber which is not hollow, it is preferable that a diameter is at least 1 μm.

In order to avoid a non-specific adsorption of a blood corpuscle on passing blood through the adsorbent of the invention, the adsorbent may be coated with a polymer which is superior in blood compatibility, for example, a polymer of hydroxy ethyl(metha)acrylate. Such coating can be done in order to prevent production of a fine particle from the adsorbent.

Then, an adsorber of TNF-α, which comprises the adsorbent of the present invention, is explained with referring to FIG. 1 that is a schematic cross section of one example of the invention.

In FIG. 1 represents an inlet for a body fluid, 2 represents an outlet for a body fluid, 3 represents an adsorbent of TNF-α of the invention, 4 and 5 represent a filter for preventing the adsorbent from flowing out, thereby a body fluid and a component contained the body fluid can pass but the adsorbent of TNF-α cannot pass, 6 represents a column and 7 represents an adsorber of TNF-α.

There is no limitation in particular in a shape and material of a container of the above adsorber for TNF-α. Examples of the container include a cylindrical column with a capacity of 150 to 400 ml and a diameter of 4 to 10 cm.

The present invention is explained in detail by means of the following EXAMPLES, however, the invention is not limited to the following EXAMPLES.

REFERENCE EXAMPLE 1

Each of cylindrical columns of glass (9 mm in inner diameter, 150 mm in length of the column) equipped with filters having a pore size of 15 μm on both ends, was charged uniformly with an agarose gel (Biogel A-5m made by BIO-RAD, 50 to 100 meshes in particle size), a vinyl polymer gel (TOYOPEARL HW-65 made by TOSOH Corporation, 50 to 100 μm in particle size) or a cellulose gel (CELLULOFINE GC-700m made by CHISSO CORPORATION, 45 to 105 μm in particle size). And then, each of relationships between flow rate and pressure loss ΔP was determined by passing water through each of columns with a peristaltic pump. The results are shown in FIG. 2.

Figure 2:
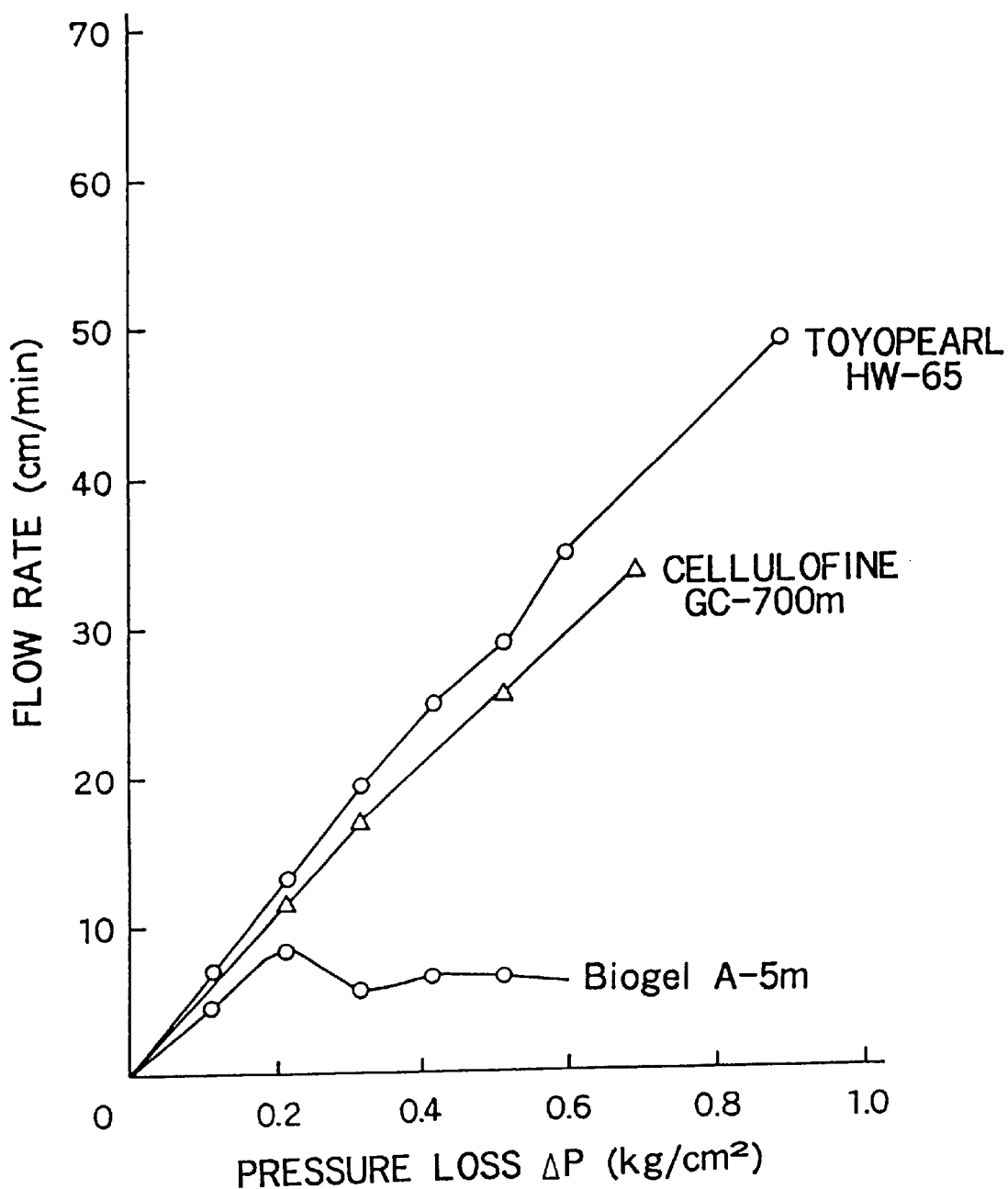
FIG. 2 is a graph showing the result of examinating the relationship between the flow rate and the pressure loss ΔP by using three kinds of water-insoluble carriers.

As shown in FIG. 2, it is realized that each flow rate in the cases of TOYOPEARL HW-65 and CELLULOFINE GC-700m increases almost in proportion as the pressure increases. On the other hand, it is realized that Biogel A-5m causes the compaction and the flow rate does not increase if the pressure is increased.

In the present invention, as the former, the gel in which the relationship between the pressure loss ΔP and the flow rate is in linear relationship up to 0.3 kg/cm$^2$ is defined as a hard gel.

EXAMPLE 1

Preparation of the adsorbent: In a reaction vessel were mixed 100 ml of cellulose beads CK-A3 (made by CHISSO CORPORATION, 5×10$^7$ in molecular weight of exclusion limit for a globular protein), 100 ml of water, 50 ml of 2N sodium hydroxide and 20 ml of epichlorohydrin, and reacted for 2 hours at 40° C. to obtain epoxidated cellulose beads CK-A3. In a reaction vessel, 100 ml of the resulting epoxidated cellulose beads CK-A3, 100 ml of water and 10 ml of 28% ammonia water were mixed and reacted over night at room temperature to obtain aminodated cellulose beads CK-A3.

On the other hand, 10 g of poly(sodium styrenesulfonate) (7×10$^4$ in average molecular weight), 1 ml of thionyl chloride and 250 ml of toluene were mixed in a reaction vessel and reacted for 8 hours at room temperature to give partially chlorinated poly(sodium styrenesulfonate).

In a reaction vessel, 10 g of the resulting chlorinated poly(sodium styrenesulfonate), 100 ml of the aminodated cellulose beads CK-A3 and 100 ml of water were admixed and reacted over night at room temperature to obtain poly(sodium styrenesulfonate)-immobilized cellulose beads CK-A3. It was confirmed that poly(sodium styrenesulfonate) containing approximately 30 mmoles of the anionic functional group per 1 ml of sedimention volume, was immobilized by means of a titration method.

Evaluation of the adsorbent: The resulting poly(sodium styrenesulfonate)-immobilized cellulose beads CK-A3 were washed with physiological saline. These beads (0.5 ml) were put in a test tube, and excess physiological saline was removed. Thereto, 3 ml of human serum containing approximately 20 ng/ml of TNF-α was added and shaked for 2 hours at 37° C. The concentration of TNF-α in supernatant was measured by means of an ELISA method. The results of the analysis are shown in TABLE 1.

COMPARATIVE EXAMPLE 1

Cellulose beads CK-A3 was equilibrated with physiological saline. These beads (0.5 ml) were put in a test tube, and excess physiological saline was removed. Thereto, 3 ml of human serum containing about 20 ng/ml of TNF-α was added and shaked for 2 hours at 37° C. The concentration of TNF-α in supernatant was measured by means of an ELISA method. The results are shown in TABLE 1.

COMPARATIVE EXAMPLE 2

Preparation of the adsorbent: In a reaction vessel were mixed 100 ml of cellulose beads CK-A3, 100 ml of water, 50 ml of 2N sodium hydroxide and 20 ml of epichlorohydrin, and reacted for 2 hours at 40° C. to obtain epoxidated cellulose beads CK-A3. 6 g of sodium dextran sulfate and 100 ml of water (the concentration of sodium dextran sulfate was approximately 2.5%) were added into 100 ml of the resulting epoxidated cellulose beads CK-A3, and adjusted to pH 11 and shaked for 16 hours at 45° C. And then, the resulting gel was filtered off and washed with water to obtain sodium dextran sulfate-immobilized cellulose beads CK-A3. It was confirmed that sodium dextran sulfate containing approximately 30 mmoles of the anionic functional group per 1 ml of sedimentation volume, was immobilized by means of a titration method.

Evaluation of the adsorbent: The resulting sodium dextran sulfate-immobilized cellulose beads CK-A3 were washed with physiological saline. These beads (0.5 ml) were put in a test tube, and excess physiological saline was removed. Thereto, 3 ml of human serum containing approximately 20 ng/ml of TNF-α was added and shaked for 2 hours at 37°. The concentration of TNF-α in supernatant was measured by means of an ELISA method. The results of the analysis are shown in TABLE 1.

TABLE 1

|  | Concentration of TNF-α in supernatant |
| --- | --- |
| EX. 1 | 16 ng/ml |
| COM. EX. 1 | 21 ng/ml |
| COM. EX. 2 | 21 ng/ml |

It is easily found that the concentration of TNF-α in EXAMPLE 1 decreases compared with that in COMPARATIVE EXAMPLE 1 and that TNF-α in a body fluid can be efficiently adsorbed and removed by using the adsorbent of the present invention. In contrast, it is found, from COMPARATIVE EXAMPLE 2, that TNF-α cannot be adsorbed by the adsorbent wherein a compound merely having an anionic functional group X, sodium dextran sulfate, is immobilized and that X which is bonded to a benzene ring is necessary.

EXAMPLE 2

A column (made by BIO-RAD, 10 mm in inner diameter, 100 mm in length of the column) was charged with 2 ml of poly(sodium styrenesulfonate)-immobilized cellulose beads CK-A3 obtained in EXAMPLE 1 and washed with physiological saline. And then, therethrough was passed 5.3 ml of human serum containing approximately 20 ng/ml of TNF-α at a flow rate of 0.33 ml/min and subsequently 5 ml of physiological saline was passed at the same flow rate. During such procedure, the resulting eluent from the outlet of the column was collected, in which firstly 0.33 ml of each fraction was collected 16 times, subsequently 1 ml of each fraction was collected twice and finally 3 ml of fraction was collected once. The concentration of TNF-α in the resulting each fraction was measured by means of an ELISA method and the concentration of protein was also measured by employing BCA Protein Assay Reagent (made by PIERCE). The results are shown in FIG. 3.

Figure 3:
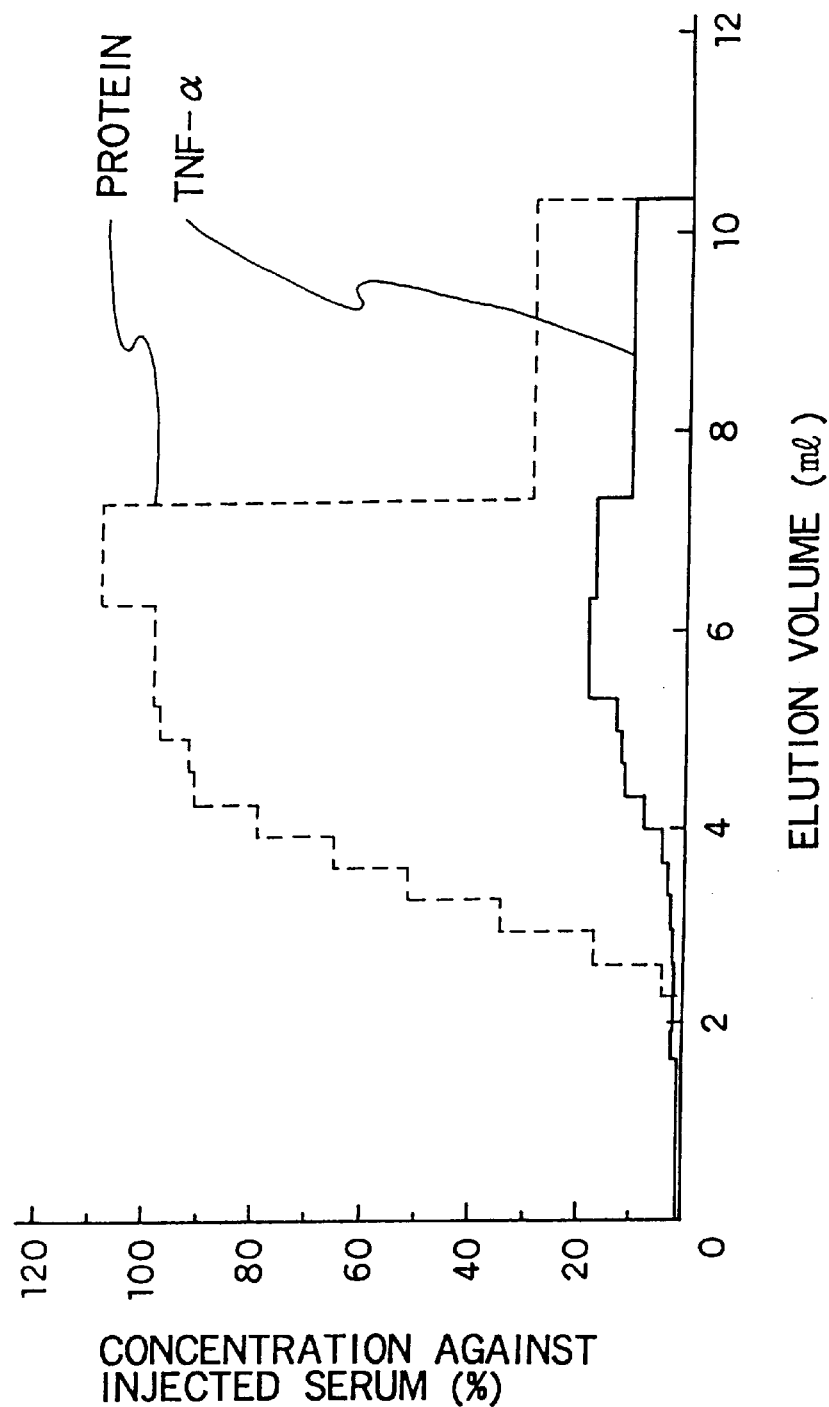
FIG. 3 is a graph showing the change of the concentration of TNF-α and protein in the elution liquid when serum containing TNF-α was flowed through the adsorber for adsorbing TNF-α of EXAMPLE 2, wherein a column is charged with cellulose beads CK-A3 onto which polystyrenesulfonic acid is immobilized.

The concentration of TNF-α or protein in each fraction in FIG. 3 is represented as a percentage when the concentration of TNF-α or protein in injected serum is 100.

COMPARATIVE EXAMPLE 3

Preparation of the adsorbent: In a reaction vessel were mixed 100 ml of CELLULOFINE GC-700m (made by CHISSO CORPORATION, $4\times10^5$ in molecular weight of exclusion limit for a globular protein), 100 ml of water, 50 ml of 2N sodium hydroxide and 20 ml of epichlorohydrin, and reacted for 2 hours at 40° C. to obtain epoxidated CELLULOFINE GC-700m. 6 g of sodium dextran sulfate and 100 ml of water (the concentration of sodium dextran sulfate was approximately 2.5%) were added into 100 ml of the resulting epoxidated CELLULOFINE GC-700m and adjusted to pH 11 and shaked for 16 hours at 45° C. And then, the resulting gel was filtrated off and washed with water to obtain sodium dextran sulfate-immobilized CELLULOFINE GC-700m. It was confirmed that sodium dextran sulfate containing approximately 30 mmoles of the anionic functional group per 1 ml of sedimentation volume was immobilized by means of a titration method.

Evaluation of the adsorbent: A column (made by BIO-RAD) was charged, in the same way as in EXAMPLE 2, with 2 ml of the resulting sodium dextran sulfate-immobilized CELLULOFINE GC-700m and washed with physiological saline. And then, therethrough was passed 5.3 ml of human serum containing approximately 20 ng/ml of TNF-α at a flow rate of 0.33 ml/min and subsequently 5 ml of physiological saline was passed at the same flow rate. During such procedure, the resulting eluent from the outlet of the column was collected in the same way as EXAMPLE 2 and the concentration of TNF-α in each fraction was measured by means of an ELISA method and the concentration of protein was also measured. The results are shown in FIG. 4.

The concentration of TNF-α or protein in each fraction in FIG. 4 is represented as a percentage when the concentration of TNF-α or protein in injected serum is 100.

It seems that TNF-α is apparently adsorbed, because the first elution of TNF-α is slow compared with that of protein in COMPARATIVE EXAMPLE 3 as shown FIG. 4. However, it is found that with passing serum the concentration of TNF-α in eluent exceeds that of protein in serum and that on passing subsequent physiological saline more TNF-α is eluted than protein. It is realized eventually that almost all amount of TNF-α is eluted comparing protein with TNF-α in the area of the graph.

Namely, it is found that TNF-α is not adsorbed practically in COMPARATIVE EXAMPLE 3 and the adsorbent thereof cannot be used actually.

On the other hand, it is found that the concentration of TNF-α in eluent hardly increases in FIG. 3 and that TNF-α can surely be adsorbed and removed.

INDUSTRIAL APPLICABILITY

Using the adsorbent of the present invention on adsorbing and removing TNF-α in a body fluid, TNF-α can be efficiently adsorbed and removed compared with a conventional adsorbent.

Also, using the adsorber of the invention which is charged with the adsorbent of the invention on adsorbing and removing TNF-α in a body fluid, TNF-α can be continuously adsorbed and removed.

What is claimed is:

1. A process for adsorbing and removing tumor necrosis factor-α, which comprises contacting a body fluid containing tumor necrosis factor-α with an adsorbent of tumor necrosis factor-α, the adsorbent comprising a water-insoluble carrier having immobilized thereon a polystyrenesulfonic acid.

2. The process of claim 1, wherein the water-insoluble carrier is hydrophilic.

3. The process of claim 1, wherein the water-insoluble carrier has a hydroxyl group.

4. The process of claim 1, wherein the water-insoluble carrier is porous.

5. The process of claim 1, wherein the water-insoluble carrier is a porous cellulose gel.

* * * * *